(12) United States Patent
McIver

(10) Patent No.: US 8,722,356 B2
(45) Date of Patent: May 13, 2014

(54) SAMPLING SYSTEM AND METHOD

(75) Inventor: Dawn E. McIver, Crown Point, IN (US)

(73) Assignee: MicroWorks, Inc., Crown Point, IN (US)

( * ) Notice: Subject to any disclaimer, the term of this patent is extended or adjusted under 35 U.S.C. 154(b) by 1817 days.

(21) Appl. No.: 11/771,327

(22) Filed: Jun. 29, 2007

(65) Prior Publication Data

US 2009/0004688 A1 Jan. 1, 2009

(51) Int. Cl.
*C12Q 1/24* (2006.01)
*B65D 79/02* (2006.01)
*A61B 19/00* (2006.01)
*A61B 19/02* (2006.01)
*B65D 71/00* (2006.01)
*C12Q 1/04* (2006.01)
*C12Q 1/06* (2006.01)

(52) U.S. Cl.
USPC ........... 435/30; 435/34; 435/39; 435/975; 206/223; 206/439; 206/539; 206/570; 206/572

(58) Field of Classification Search
USPC ........... 206/223, 439, 539, 570, 571, 572; 435/30, 34, 39, 975
See application file for complete search history.

(56) References Cited

U.S. PATENT DOCUMENTS

| 4,312,950 | A * | 1/1982 | Snyder et al. | 600/572 |
|---|---|---|---|---|
| 6,193,932 | B1 * | 2/2001 | Wu et al. | 422/28 |
| 6,291,171 | B1 * | 9/2001 | Ricciardi et al. | 435/6.11 |
| 2004/0241824 | A1 * | 12/2004 | Schrenzel et al. | 435/252.3 |
| 2007/0065893 | A1 * | 3/2007 | Carte et al. | 435/18 |

OTHER PUBLICATIONS

NIOSH Manual of Analytical Methods (NMAM), Fourth Edition. 1998. Aerobic Bacteria by GC-FAME 0801, Method: 0801, Issue 1, pp. 1-4.*
Biomerieux Industry, press release, http://wwwbiomerieux. comprinted, Apr. 5, 2007.
Medical Device Link, breathable bags and pouches, website, Jan. 26, 2007, www.devicelink.com.

* cited by examiner

*Primary Examiner* — Jon P Weber
*Assistant Examiner* — Kailash C Srivastava
(74) *Attorney, Agent, or Firm* — Beem Patent Law Firm

(57) ABSTRACT

A sampling system and method may use a kit that has a package enclosing a swab and a receptacle. The swab may have a shaft and a tip. The tip may be substantially made of calcium alginate. The receptacle may contain a diluent, such as sodium citrate, and glass beads. The swab may be used in an environment to sample microorganisms present on surfaces or in equipment. The kit may be used in a method of sampling and the resulting sample may be used in a method of quantitative testing.

7 Claims, 2 Drawing Sheets

SAMPLING SYSTEM AND METHOD

BACKGROUND OF THE INVENTION

1. Field of Invention

This invention pertains to a sampling system and method. More particularly, this invention pertains to a microbiological sampling system and method using swabs.

2. Description of the Related Art

Microbiological sampling is a means of ascertaining the presence of microorganisms in an environment. The microorganisms may be bacteria, viruses, fungi, or other organisms. Sampling may be done by contacting a sterile swab with the item to be sampled. The sample may then be tested in a laboratory. Sampling tests are typically qualitative tests, used to determine whether microorganisms are present.

Sampling using a swab is performed in hospitals, pharmaceutical clean rooms, and in isolator systems as part of an overall environmental monitoring program. Swab sampling is sometimes intended to detect microorganisms that may be trapped in hard to reach places such as on equipment with irregular surfaces or on conveyer belts, tracks for vials, etc. Doctors and health professionals use swab sampling systems and methods in clinics and hospitals on patients for certain tests, such as for swabbing a throat for testing for Group A *Streptococcus* bacteria for strep throat.

Swab sampling is also performed by pharmaceutical companies as part of a cleaning validation program. Cleaning validation is done to show that cleaning procedures can remove residual products, cleaners and microorganisms from surfaces of product contact equipment.

Food companies, medical device companies and cosmetic companies also use swabs in order to detect microorganisms on surfaces. It would be desirable to develop a system and/or method to overcome one or more of the shortcomings in the prior art.

BRIEF SUMMARY

A sampling system and method may use a kit. A kit may comprise a receptacle and a swab. The receptacle and swab may be enclosed in a package. The receptacle may be a tube and may have a predetermined width, a diluent, a plurality of agitating surfaces, an opening, and a closure for said opening. The swab may have a tip with a predetermined width and substantially made of calcium alginate. The predetermined width of the tip may be smaller than the predetermined width of the receptacle so as to allow the tip to be enclosed in the receptacle.

In one embodiment, a method of sampling may comprise of entering an environment, opening a kit, preferably by aseptically unwrapping a package, containing the swab and the receptacle. A sleeve enclosing a swab may be unwrapped and the cap of the receptacle may be removed and the tip of the swab may be wet by dipping it in the diluent, accessing the diluent through the opening. The wet tip may be used to contact a surface in the environment, taking a sample. The cap to the receptacle may be removed to allow the tip to be placed inside the receptacle which may also contain diluent and beads, through the opening, and then the receptacle may be closed with the cap. The closed receptacle contains the sample and is protected from contamination when removed from the environment until the cap is removed for testing the sample, usually in a laboratory.

In a method of testing a sample, contents of the receptacle may be mixed using a vortex mixer to dissolve the calcium alginate on the tip. The contents of the receptacle may then be filtered using a filter. The receptacle and filter may be rinsed with a rinsing solution, preferably using multiple applications of Fluid A and a filtration unit. The filter may be transferred to media on a plate and incubated for a duration and at a temperature specific for the microorganism being investigated. Colonies appearing on the media may be counted using a colony counter and the sample may be quantitatively assessed by calculating the number of colony forming units per square area of surface sampled. The colony counter may be manual or automated.

DETAILED DESCRIPTION

Figure 1:
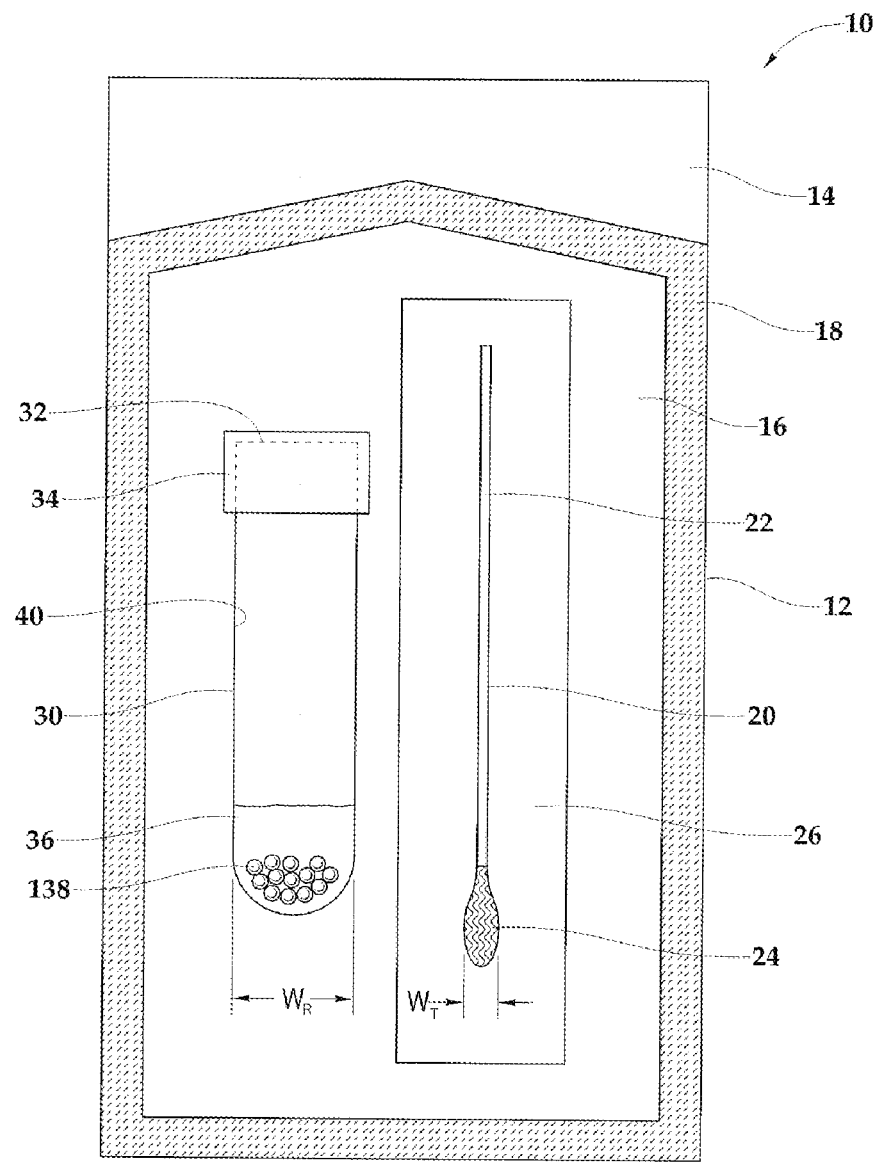
FIG. 1 is a plan view of a kit in accordance with the invention.

A sampling system and method may use a kit 10. In one embodiment, shown in FIG. 1, kit 10 may have a package 12. Package 12 may have a backing 14, a cover 16, and a seal 18, where seal 18 connects backing 14 to cover 16. Kit 10 may have a swab 20 and a receptacle 30.

Swab 20 may have a shaft 22 and a tip 24 and may be enclosed in a sleeve 26, which may be made of paper, plastic, or other material. Shaft 22 may be made of wood, paper, plastic, metal, or other rigid material and may have a round shaped cross section. Shaft 22 may have a length between about 2 inches and about 12 inches, preferably between about 4 and about 8 inches, still more preferably about 6 inches, and a diameter between about one twentieth of an inch and about one half of an inch, preferably between about one eighth of an inch and one third an inch, still more preferably about one-fourth an inch. Preferably, shaft 20 may detach, or be able to be broken, from tip 24.

Tip 24 may be at an end of swab 20 and connected to shaft 22. Tip 24 may have a predetermined width $W_T$. Tip 20 may have a width $W_T$ between about a tenth of an inch and about 2 inches, preferably between about one inch and about one sixth an inch, still more preferably about a third of an inch. Tip 24 may comprise of a material that collects a sample and dissolves in certain solutions. Tip 24 may substantially comprise of calcium alginate.

Receptacle 30 may have an opening 32 and may have a closure 34. Closure 34 may be a cap to close opening 32. Receptacle 30 may be a container, such as a vial, bag, or tube. Preferably, as shown in FIG. 1, receptacle 30 is a tube. Receptacle 30 may be substantially made of glass, plastic, metal, or ceramic, but preferably glass. Receptacle 30 may have a predetermined width $W_R$. The predetermined width $W_R$ of receptacle 30 may be larger than the predetermined width $W_T$ of tip 24. Receptacle 30 may have a width $W_R$ between about a fourth of an inch and about 4 inches, preferably between about two inches and about one half an inch, still more preferably about one inch. Receptacle 30 may have a length between about 2 inches and about 10 inches, preferably between about 3 inches and about 8 inches, still more preferably between about 4 and about 5 inches.

Receptacle 30 may have a diluent 36. Diluent 36 may be a buffer. Preferably, diluent 36 is sodium citrate. Diluent 36 may be of a predetermined quantity sufficient to dissolve materials in tip 24. The quantity of diluent 36 may be between about 1 and about 500 mL, preferably about 5 and about 100 mL, still more preferably between about 10 and 50 mL.

Receptacle 30 may have a plurality of agitating surfaces 38. Agitating surfaces 38 may increase mixing in receptacle 30. Agitating surfaces 38 may be incorporated into a wall 40 of receptacle 30 and may have contoured shapes for increasing mixing of diluent 36 when receptacle 30 is shaken. Preferably, as shown in FIG. 1, agitating surfaces 38 comprise a plurality of beads 138. Beads 138 may be substantially, or entirely, made of glass, metal, acrylic, ceramic, plastic, or other material and may be have different sizes and shapes or, preferably may be made of glass and round in shape. Beads 138 may be unattached from wall 40 and may move when receptacle 30 is shaken to increase mixing. Each bead 138 may be between about one twentieth of an inch and about one inch, preferably between about one tenth of an inch and about one half inch, still more preferably about one fourth of an inch. The diameter of each bead 138 and the number of beads 138 may vary, but preferably are predetermined to be sufficient to assist in mixing. Further, the size of receptacle 30 may influence the number and size of the beads used. Preferably, the number of beads may be between about 5 and about 35, still more preferably between about 10 and about 15 beads.

Package 12 may be sized to correspond to and enclose receptacle 30 and swab 20. In one embodiment, receptacle 30 may be about 4 and one half inches in length and about 1 and one third inches in width $W_R$. Swab 20 may be about 6 inches in length and sleeve 26 may be about 7 inches in length and about 1 and one half inches in width. Package 12 to enclose these sized materials may be about 10 inches in length, about 5 and one half inches in width, and about 1 and one half inches in thickness. Package 12 may have a length between about 5% and about 150% greater than the length of the longer of swab 20 and receptacle 30, preferably between about 10% and about 80%, still more preferably between about 20% and about 50%.

When package 12 is utilized to enclose receptacle 30 and swab 20, kit 10 may be taken into the sampling environment without having multiple independent sterilizations for the materials to be used in the sampling process. Materials inside package 12 are preferably sterile so that only the one package 12 would need to be sterilized prior to entering the environment for the sample. Vaporized hydrogen peroxide (VHP) is sometimes used to maintain sterilization in the room to be sampled, therefore, it is preferable for the package to be VHP resistant.

Figure 2:
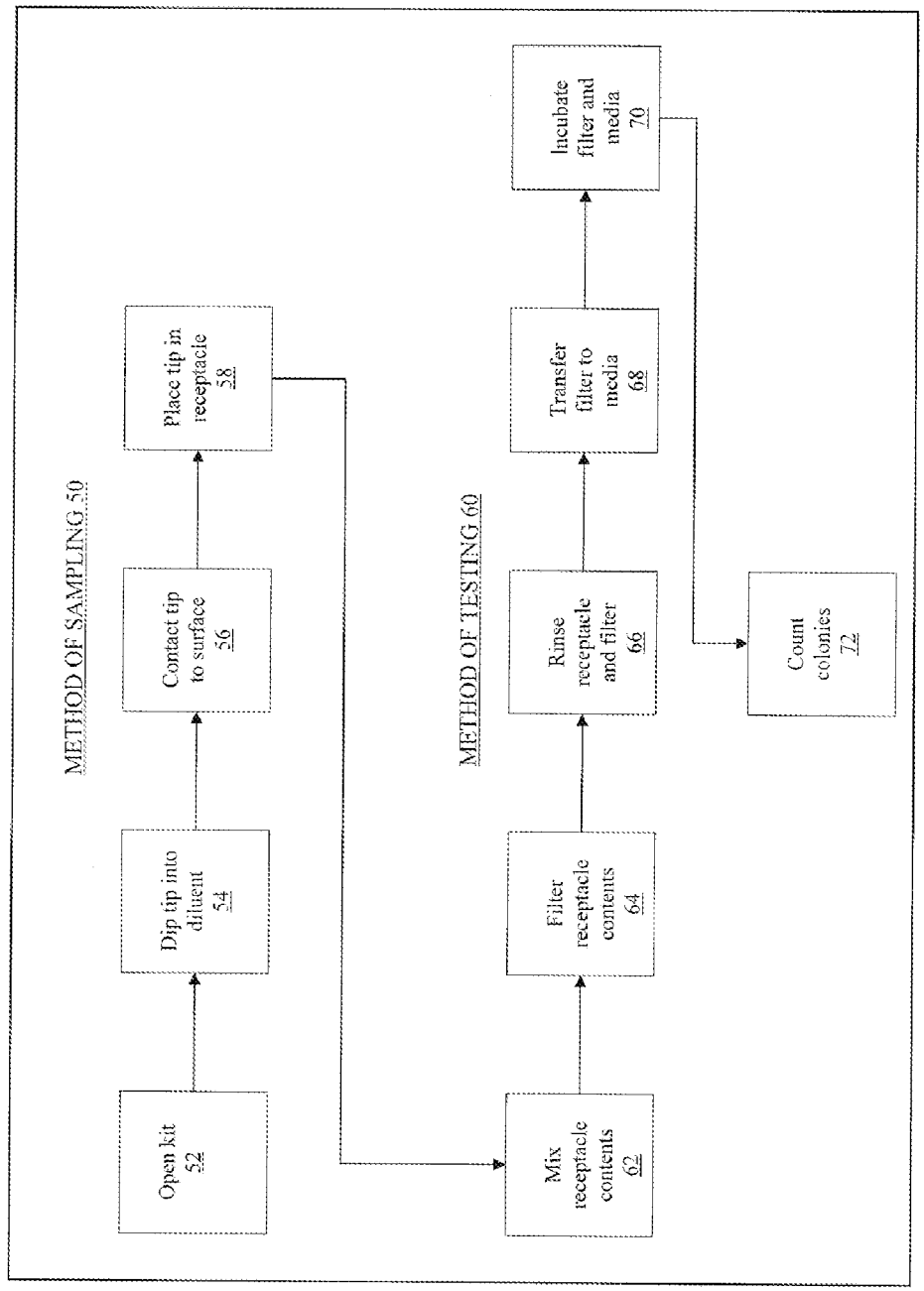
FIG. 2 is a schematic diagram of a sampling and testing method in accordance with the invention.

In one embodiment, kit 10 may be used in a method of sampling 50 and then the sample may be used in a method of testing 60 for microorganisms. As shown in FIG. 2, a method of sampling 50 may comprise of entering an environment, opening 52 a kit 10 having a swab 20 with a tip 24 and a receptacle 30 provided with a predetermined quantity of diluent 36 and, preferably, a plurality of agitating surfaces 38, dipping 54 tip 24 into diluent 36, contacting 56 tip 24 to a surface in said sampling environment, placing 58 tip 24 in receptacle 30 and closing receptacle 30.

Opening step 52 may include unwrapping sleeve 26 enclosing swab 20 and dipping step 54 may include opening the closure 34 of receptacle 30 to wet tip 24 in diluent 36 through opening 32. Contacting step 56 may include obtaining a sample of microorganisms in the sampling environment by rubbing tip 24 on a surface or in an area of a unit of equipment. Placing step 58 may include separating tip 24 from shaft 22 of swab 20 to be of a size able to be closed inside receptacle 30. Tip 24 may have calcium alginate and diluent 36 may be sodium citrate. A plurality of agitating surfaces 38 may be in the form of beads 138. The closed receptacle 30 having tip 24, which contains a sample of microorganisms, diluent 36, and agitating surfaces 38, is protected from contamination by being closed when removed from the sampling environment until opened for testing the sample, usually in a laboratory.

The sample in receptacle 30 may be tested using a method of testing 60 that may include in one embodiment, as shown in FIG. 2, mixing 62 the contents of a receptacle 30, comprising tip 24, which contains a sample of microorganisms, diluent 36, and agitating surfaces 38, filtering 64 the sample, rinsing 66 receptacle 30 and the filter with rinsing solution, transferring 68 the filter to a media, incubating 70 the media and filter, and counting 72 colonies. Receptacle 30 contents, which preferably comprises tip 24 made of calcium alginate, diluent 36, which preferably is sodium citrate, and a plurality of beads 138, may be agitated, or mixed, using a vortex mixer. Mixing step 62 may be for a duration long enough to dissolve the calcium alginate in the tip. Mixing step 62 duration may be between about 10 seconds and about 5 minutes, preferably between about 30 seconds and about 2 minutes, still more preferably about one minute.

Filtering step 64 may include a funnel. Preferably, a 0.45 micron filtration unit is used. Rinsing step 66 may include application of a rinsing solution. Rinsing solution is preferably a solution that does not interfere with the growth of microorganisms. Rinsing solution may be a peptone water, preferably a 0.1% peptone water, or Fluid A. Rinsing step 66 may include rinsing receptacle 30, filter, filtering unit, and beads 138. Preferably, rinsing step 66 comprises a multiple rinsing session, still more preferably, a rinsing session of three applications of about 10 mL of Fluid A, for a total of 30 mL.

Transferring step 68 may comprise moving the filter to a media, preferably a growth media. Media type may vary, and may vary according to the intended organism to be tested in the sample. Media may be a on a plate and preferably is Tryptic (Trypticase) Soy Agar (TSA) with lecithin and polysorbate 80.

Incubating step 70 may include using an incubator for setting a temperature suitable for promoting growth of microorganisms. The media, with the filter, may be incubated to promote the growth of the microorganisms in the sample. Incubation duration and temperature may vary, and may vary according to the intended organism to be tested in the sample. Incubation may be for between about 1 day and about 10 days, preferably between about 2 and about 5 days, and still more preferably at least 3 days, and at a temperature between about 28 degrees C. to about 37 degrees C., preferably between about 30 degrees C. to about 35 degrees C.

If the intended organism to be tested is a yeast or a mold, the media may be a sabouraud dextrose agar with lecithin and the incubation period may be for between about 3 days and about 7 days, preferably at least about 5 days, and at a temperature between about 17 degrees C. to about 28 degrees C., preferably between about 20 degrees C. to about 25 degrees C.

After incubation an estimation of the number of microorganisms on the media may be determined. Counting step 72 may include counting the colonies and may be accomplished using a colony counter. The number of colonies may be reported as a number of colony forming units (CFU) per surface area sampled. Method of testing 60 may measure quantitatively a number of microorganisms in a sample. In addition, method of testing 60 may measure a sample qualitatively for the types of microorganisms in a sample.

In one embodiment, the invention may be a quantitative test, providing results on how many organisms are present. Qualitative tests do not provide results of the number of organisms present. The combination of the beads 138 in receptacle 30, calcium alginate tip 26 that dissolves in the sodium citrate, the neutralizing effect of the sodium citrate and the testing method that includes rinsing step 66 where receptacle 30 is rinsed makes the recovery of microorganisms more effective, and, therefore, may be able to be validated to meet regulatory expectations for such a method. Diluent 36, preferably sodium citrate, may neutralize many of the sanitizers used in the pharmaceutical industry, which means that the method may be validated and shown to recover at least 70% of the microorganisms present on the surface being sampled. Such a recovery complies with requirements for the validation of microbiological methods for use in the pharmaceutical industry.

Kit 10 may be in a self-contained, sterilizable, VHP resistant package 12 that is ready to be taken into a sampling environment, such as a cleanroom or isolator. Having kit 10 in one package 12 saves time and cost of sterilizing and reduces the risk that the packaging or sampling materials bring contamination into the environment to be sampled. The VHP resistant package 12 prevents residual VHP sterilant, used to sterilize the inside of isolators, from penetrating into the packaging and contacting swab 20. If the VHP were to contact swab 20, swab 20 would be ineffective for its use for sampling because it would contain a sterilant that could affect the microorganisms in the sample.

Multiple kits 10 may be used in a single environment for additional sampling and testing. Generally, multiple kits 10 are used for a single environment to sample and test different surfaces or equipment in that environment.

EXAMPLE

In one embodiment, kit 10 has a package 12 with a backing 14, a cover 16, and a seal 18 that connects 14 backing to cover 16. Enclosed in package 12 are a swab 20 and a receptacle 30. Swab 20 has a shaft 22 and a tip 24 and is enclosed in a sleeve 26. Tip 24 is substantially made of calcium alginate. Receptacle 30 has an opening 32 and a closure 34, which is a cap, to close opening 32. Receptacle 30 has about 20 mL of diluent 36, preferably sodium citrate, and a plurality of agitating surfaces 38, preferably glass beads 138. Predetermined number of beads 138 to increase mixing in receptacle 30 is about 12 to about 15.

A method of sampling 50 and a method of testing 60 a sample utilize kit 10. Method of sampling 50 includes entering an environment to be tested and opening 52, which is a sterilized package containing a swab 20 and a receptacle 30. Swab 30 has shaft 22 and a calcium alginate tip 24 and receptacle 30 has a predetermined quantity of a diluent 36, sodium citrate, and a plurality of agitating surfaces 38, glass beads 138. Tip 24 is dipped 54 into the diluent 36 and then tip 24, now wet, is contacted 56 with a surface or piece of equipment in the environment. Tip 24 is broken from shaft 22 and placed 58 into receptacle 30. Receptacle 30 is sealed with a closure 34 and may exit the environment to be taken to a laboratory for testing the sample.

In a method of testing 60, the contents of receptacle 30 are mixed 62 using a vortex mixer to dissolve the calcium alginate on the tip 24. The contents of receptacle 30 are filtered 64 using a filter. Receptacle 30 and filter are rinsed 66 with a rinsing solution, using multiple applications of Fluid A and a filtration unit. The filter is transferred 68 to media on a plate and incubated 70 for a duration and at a temperature specific for the microorganism being investigated. Colonies appearing on the media may be counted 72 using a colony counter and reported as a number of colony forming units per surface area sampled.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A sterile kit for obtaining and preparing a live microbiological sample, comprising:
   a receptacle; and
   a swab;
   wherein said receptacle and said swab are enclosed in a package;
   said package having a backing, a cover, and a seal that connects said backing to said cover; and
   wherein said package is impervious to vaporized hydrogen peroxide;
   said receptacle having a predetermined width, a diluent, a plurality of beads,
   an opening, and a closure for said opening; and
   said swab having a tip with a predetermined width;
   wherein said predetermined width of said tip is smaller than said predetermined width of said receptacle.

2. A kit according to claim 1, wherein said tip is substantially made of calcium alginate.

3. A kit according to claim 1, wherein said diluent is sodium citrate.

4. A kit according to claim 1, wherein each of said plurality of beads is substantially made of a material selected from the group consisting of:
   glass;
   metal;
   ceramic; and
   plastic.

5. A kit according to claim 1, wherein:
   said swab is enclosed in a sleeve;
   said tip has calcium alginate;
   said receptacle has sodium citrate; and
   said plurality of beads is a plurality of glass beads.

6. A kit according to claim 1, wherein said plurality of beads have diameter between about one-twentieth of an inch and about one inch.

7. A kit according to claim 1, wherein said plurality of beads have diameter between about one-tenth of an inch and about one-half an inch.

* * * * *